United States Patent
Briot et al.

(10) Patent No.: US 6,627,781 B1
(45) Date of Patent: Sep. 30, 2003

(54) PROCESS FOR PRODUCING, JOINTLY OR OTHERWISE, MONOALKYL AROMATIC COMPOUNDS, DIALKYL AROMATIC COMPOUNDS AND TRIALKYL AROMATIC COMPOUNDS

(75) Inventors: Patrick Briot, Pommier de Beaurepaire (FR); Pierre Yout, Vienne (FR); Jean-Claude Hipeaux, Colombes (FR); Eric Benazzi, Chatou (FR); Leon Lew, Caracas (VE)

(73) Assignees: Institut Francais du Petrole, Cedex (FR); Industrias Venoco C A, Caracas (VE)

(*) Notice: Subject to any disclaimer, the term of this patent is extended or adjusted under 35 U.S.C. 154(b) by 0 days.

(21) Appl. No.: 09/671,295

(22) Filed: Sep. 27, 2000

(30) Foreign Application Priority Data

May 2, 2000 (FR) .............................. 00 05677

(51) Int. Cl.$^7$ .............................. C07C 2/64; C07C 2/66
(52) U.S. Cl. .................................................. 585/449
(58) Field of Search ................................ 585/449, 475, 585/470

(56) References Cited

U.S. PATENT DOCUMENTS

| | | | | |
|---|---|---|---|---|
| 2,400,437 A | | 5/1946 | Perkins et al. ............. 585/447 |
| 3,184,517 A | * | 5/1965 | Lee et al. ................... 585/449 |
| 4,107,224 A | * | 8/1978 | Dwyer ........................ 585/449 |
| 4,459,426 A | * | 7/1984 | Inwood et al. .............. 585/323 |
| 4,520,218 A | * | 5/1985 | Berg et al. .................. 585/449 |
| 5,003,119 A | * | 3/1991 | Sardina et al. ............. 585/323 |
| 5,030,785 A | * | 7/1991 | Huss et al. ................. 568/681 |
| 5,198,595 A | * | 3/1993 | Lee et al. ................... 585/467 |

* cited by examiner

Primary Examiner—Thuan D. Dang
(74) Attorney, Agent, or Firm—Millen, White, Zelano, Branigan, P.C.

(57) ABSTRACT

Process for the production of at least one compound that is selected from among monoalkyl aromatic compounds, dialkyl aromatic compounds and trialkyl aromatic compounds by alkylation or transalkylation of an aromatic compound by at least one alkylating agent that is selected from among the olefins, whereby the process is characterized in that it is carried out in one or two stages, involving two reaction zones in series, whereby one of these two zones can be switched off so as to be able, depending on whether or not one of the zones is switched off, to meet the demand either of the three types of mono, di- and trialkyl aromatic compounds, or two of these types or a single one of the types of mono- or di- or trialkyl aromatic compounds.

31 Claims, 2 Drawing Sheets

PROCESS FOR PRODUCING, JOINTLY OR OTHERWISE, MONOALKYL AROMATIC COMPOUNDS, DIALKYL AROMATIC COMPOUNDS AND TRIALKYL AROMATIC COMPOUNDS

CROSS-REFERENCE TO RELATED APPLICATION

This application may be related to Applicants' concurrently filed application Ser. No. 09/671,294, entitled "Synthetic Oil With A High Viscosity Number And A Low Pour Point", based on French Application 00/05.676 filed May 2, 2000.

FIELD OF THE INVENTION

The process that is the object of this application is a process for alkyations or transalkylating aromatic compounds for the purpose of producing alkylaromatic compounds. The aromatic monoalkyls find a use in the composition of gasolines or lyes, aromatic dialkyls and trialkyls in the field of lubricants.

The process according to the invention thus makes possible the production of mono-, di- and trialkyl aromatic compounds. This process thus relates to the alkylation of aromatic compounds (benzene, toluene, cumene) by alkylating agents (olefins, alcohol, halides) for producing aromatic monoalkyls whose grafted aliphatic chain comprises a carbon number that is selected from 2 to 20 carbon atoms.

BACKGROUND OF THE INVENTION

This process can also produce dialkylbenzenes, i.e., aromatic compounds where the benzene core comprises two paraffin chains whose carbon atom number can be identical or different. Each of these aliphatic chains can contain 2 to 20 carbon atoms. In the case where it would be desired to produce aromatic trialkyls, there are three aliphatic chains of which two, for example, have identical lengths.

The alkylation of aromatic compounds has been known for many years.

U.S. Pat. No. 2,939,890 (Universal Oil Products Company), dating from 1960, thus claims a process or synthesis or cumene by using BF3 as a catalyst.

U.S. Pat. No. 3,173,965 (Esso Research), dating from 1965, which claims as suitable catalysts for the alkylation of benzene acids of type AlCl3, AlBr3, FeCl3, SnCl4, BF3, H2SO4, P2O5 and H3PO4is also known.

In the same connection, U.S. Pat. No. 4,148,834 (1979) and U.S. Pat. No. 4,551,573 (1985) claim the use for the first of HF during the first stage and AlCl3 or AlBr2 in the second stare. The second patent claims, more particularly, a mixture of aluminum halides and elementary iodine.

U.S. Pat. No. 3,251,897 claims the use of X and Y zeolites that are exchanged with rare earths for the production of monoalkyl benzene (ethylbenzene, cumene) and diethylbenzene.

U.S. Pat. No. 3,631,120 (1971) claims the use of zeolites, mainly Y zeolite, having a silica to alumina ratio of 4 to 4.9 for the production of cumene.

U.S. Pat. No. 5,107,048 (1992) claims the use of an amorphous catalyst of the silica type promoted as Lewis acid using BF3.

SUMMARY OF THE INVENTION

The process, claimed by the applicant, relates to the production of monoalkyl benzene and/or dialkyl benzene and/or trialkyl benzene and has as original features:

- a production flowsheet that is flexible and that makes it possible to adapt it to the needs of the market or to the possibilities of supply,
- the catalysts that are used are neither dangerous nor toxic as are the aluminum halides or HF,
- their specificity is such that it makes it possible to obtain products of high purity,
- the catalysts that are used in this invention can be regenerated by simple combustion with air or under oxygen or referenced by a treatment under hydrogen.

The invention is therefore essentially characterized by a flexible process that normally comprises in series two combined stages that are suitable for producing, jointly or otherwise, mono-, di- and trialkyl aromatic compounds.

Process in which based on the desired products, either the two stages or the first or the second of these two stages, whereby each of the stages can be switched off or restarted at any time, can be used based on the requirements of the clientele to be supplied in mono-, di- or trialkyl aromatic compound that are obtained by alkylation or by transalkylation of an aromatic hydrocarbon by an olefinic compound.

The three types of products that can be produced by the process of which the applicant claims the property correspond to the following generic chemical formulas:

Monoalkyl benzene:

R1 = aliphatic chain that then comprises 2 to 20 carbon atoms

Dialkyl benzene:

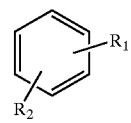

These alkyl chains each have 2 to 20 carbon atoms. These chains can have equal dimensions or different lengths.

The products that are obtained consist of three isomers: ortho, meta and para.

Trialkyl benzene:

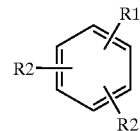

Here, aliphatic chains R1 and R2 can have identical or different lengths and comprise 2 to 20 carbon atoms.

DESCRIPTION OF THE PROCESS

In the process, four different types of production can be considered separately when only a single specific product is desired:

Case 1: Production of dialkyl benzene for which the aliphatic chains are of different lengths, Case 2: Production of dialkyl benzene for which the aliphatic chains are of identical length, Case 3: Production of monoalkyl benzene,
Case 4: Production of trialkyl benzene.

Two main reaction types occur:

Alkylation:

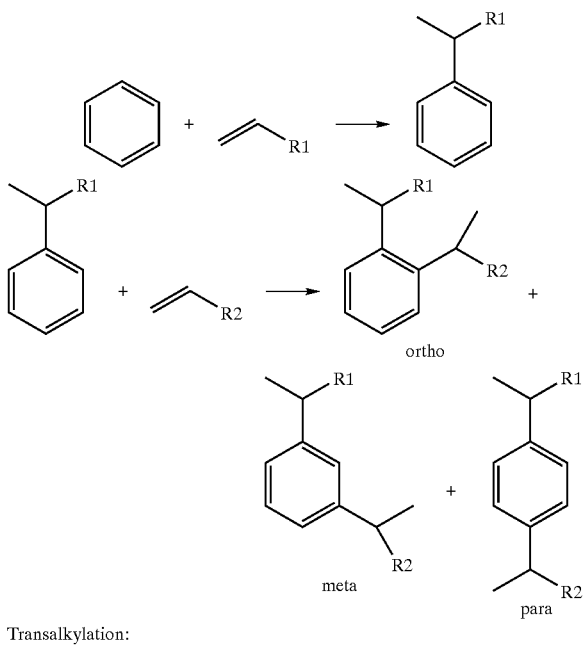

Transalkylation:

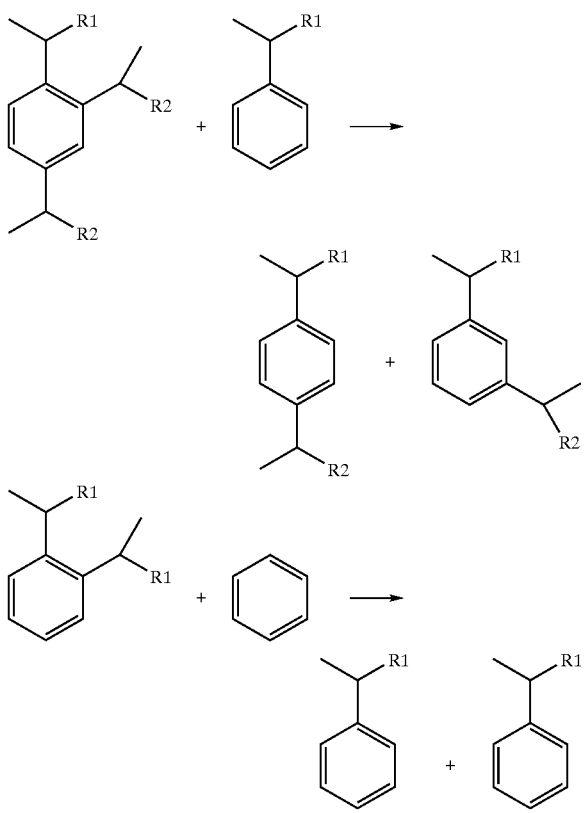

BRIEF DESCRIPTION OF THE DRAWINGS

A simplified diagram of the process is presented in FIG. 1. It consists of two stages a and b that can be separated or overlapped.

Figure 1:
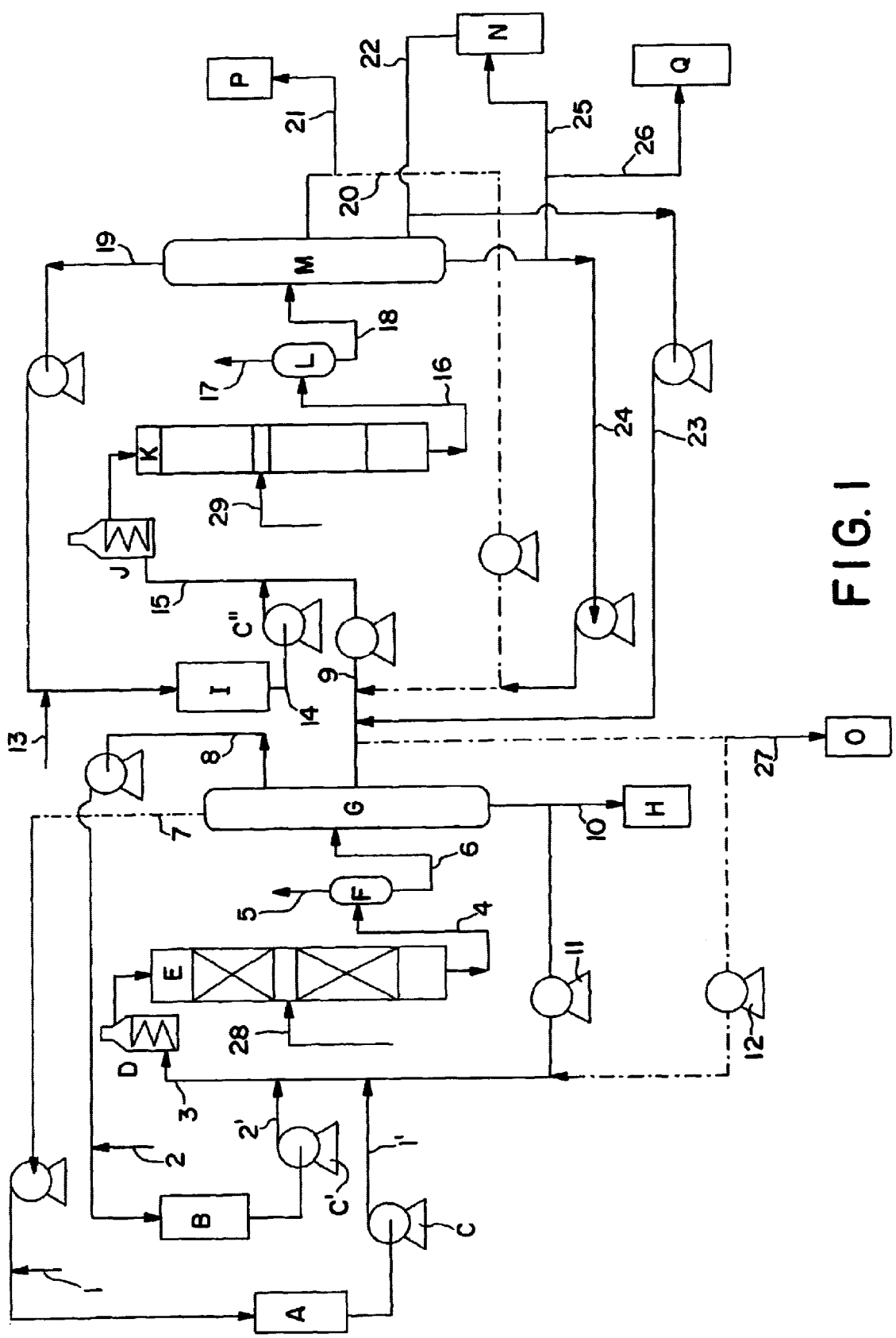

In the description of the process that is given below to simplify understanding, the aromatic compound will be called benzene and the alkylating agent will be called olefin (olefin 1 or olefin 2).

In stage a, the aromatic compound (or benzene) is transported via line 1 up to a supply tank A. The alkylating agent (or olefin 1) is routed via line 2 to a supply tank B. These two products are then sent into a line 3 using pumps C and C' and lines 1' and 2'. The reagents are then preheated to the reaction temperature using a furnace D. The hot reagents are then injected into a reactor E that contains catalyst No. 1. The characteristics of this catalyst will be related in more detail below. The alkylation reaction is exothermic, hence it may be useful to inject a portion of the aromatic compound (or a portion of olefin 1) between the different beds of the reactor, if there are several beds, via line 28. The products of the reaction are routed via line 4 to a gas-liquid separator F that makes it possible to separate the gases (line 5) and the liquid (line 6).

This liquid effluent is then sent into at least one distillation column (G) in which will be separated:
  the unconverted aromatic compound (benzene) that will be recycled in tank A via line 7,
  the unconverted alkylating agent (olefin 1) can be recycled in tank B via line 8,
  the monoalkyl aromatic compound (or monoalkyl benzene) can be, depending on the case:
    case 1 or case 4, defined above, sent in the second part of the process (i.e., in second stage (b)) via line 9,
    case 2: recycled at the inlet of reactor E via pump 12 to undergo a second alkylation,
    case 3: recovered via line 27 and stored as product in a tank O,
  the dialkylaromatic compound (or dialkyl benzene) can be depending on the case:
    Case 1 or 3: recycled via pump 11 then 3 at the inlet of the reactor to undergo a transalkylation,
    Case 2: recovered using line 10 and stored in a tank H.

This distillation column G in the example advantageously can be replaced by a column succession that can operate at different pressures (2 to 4 columns).

In stage b (case 1), the monoalkyl aromatic compound (monoalkyl benzene) of line 9 is mixed with alkylating agent 2 (or olefin 2) that is obtained from line 13, of tank 1 via pump C". The mixture is preheated in furnace J and penetrates inside reactor K that contains the second catalyst (catalyst No. 2) via line 15. The reaction being exothermic, it may be prudent to inject a portion of olefin 2 between the beds of the reactor (if there are several beds) via line 29 to control the temperatures. The effluents of the reactor (line 16) go into a gas-liquid separator L. The gases are evacuated via line 17.

The liquid effluent is sent via line 18 to a distillation column M. The different products at the end of the distillation are:
  at the top of the column, unconverted alkylating agent 2 (or olefin 2) that will be recycled (line 19) at the inlet of the reactor using a supply tank I,
  the monoalkyl that is obtained from the first reactor and is not converted will be treated differently depending on the case. In case 1, it will be recycled at the inlet of the second reactor with line 20. In the case where a joint production of dialkyl benzene and monoalkyl benzene is desired, it can be stored in a tank P via line 21, the dissymmetrical dialkyl benzene is sent for storage into a tank N via line 22. However, if the desired production is of trialkyl benzene (case 4), it is possible to recycle it via line 23 at the inlet of the second reactor to undergo a new alkylation.

the trialkylbenzene will be, depending on the case: recycled at the inlet of the second reactor via line 24 to undergo a transalkylation, stored as a product in a tank Q via line 26, or then mixed with the dialkyl production in tank N via line 25.

As above, this distillation column M can be advantageously replaced by a succession of distillation columns (2 to 4 columns) that can operate at different pressures.

The catalyst of stage a) can be in the form of balls, but it is most often in the form of extrudates. It consists of an acid solid that is mixed with an amorphous phase. The acid solid in question is shaped using a matrix, which is an amorphous phase. The acid solid is preferably at least one zeolite. FAU-structural-type zeolites and more particularly the Y zeolite, MOR-structural-type zeolites (the mordenite zeolite) that are synthesized in basic classic medium or else in fluoride medium (reference Patent IFP), the EUO-structural-type zeolites, i.e., the EU-1, ZSM-50, TPZ-3 zeolites), the NU-87 zeolite (if NES-structural-type, will preferably be selected. All of these zeolites are described in the document "Atlas of Zeolite Structure Types," W. M. Meier, D. H. Olso and Ch. Baerlocker, 1996 Elsevier. Among the zeolites that are preferred and can be used in the catalyst, the NU-86 zeolite that is described in Patent EP 463 768 A, the NU-85 zeolite that is described in Patent EP 462 745 A, the NU-88 zeolite that is described (French filing 96/10,507) and the IM-5 zeolite that is described in the parent (French filing 96/12,873) a also present. These zeolites are at least partly in acid form (H') but can also contain cations other than H' such as alkalines, alkaline-earths, . . . The zeolite content in the catalyst is between 5 and 95% by weight, preferably between 10 and 90% relative to the final catalyst. The overall Si/Al ratio of these zeolites is between 2.6 and 200, preferably between 5 and 100, and even more preferably between 5 and 80.

The matrix of the catalyst is a substrate that is selected from the group that is formed by alumina, silica, and silica-alumina, alumina-boron oxide, magnesia, silica-magnesia, zirconia, titanium oxide, clay, silica-magnesia, zirconia, titanium oxide, clay, whereby these compounds are used alone or in mixtures. An alumina substrate is preferably used.

The B.E.T. surface area of catalyst 1 used in stage a) is between 50 and 900 m²/g, preferably between 100 and 700 m²/g. The final Na/Al ratio of the catalyst is less than 5% atomic and preferably less than 2%.

Metal elements, such as, for example, the metals of the family of rare earths, in particular lanthanum and cerium, or the metals of group VIB of the periodic table, such as molybdenum, or noble metals or non-noble metals of group VIII, such as platinum, palladium, ruthenium, rhodium, iridium, iron and other metals such as manganese, zinc, and magnesium, can optionally be added to the catalyst (zeolite|matrix). These metal elements can be placed either on the matrix or on the zeolite phase. A certain number of catalysts have been tested. Table 1 groups the characteristics of some of them.

TABLE 1

Characteristics of Several Tested Catalysts

| Reference Catalysts | A | B | C | D |
| --- | --- | --- | --- | --- |
| Zeolitic nature | mordenite | mordenite | Eu-1 | Nu-87 |
| Content by weight of zeolite (% by weight) | 20% | 80% | 60% | 70% |
| Content by weight of alumina (% by weight) | 80% | 20% | 40% | 30% |
| Si/Al (Fx) of zeolite | 38 | 40–50 | 36 | 33 |
| B.E.T. surface area (m²/g) | 475 | 483 | 444 | 483 |
| Na/Al (% atomic) | 0.8 | 1.02 | 0.1 | 0.6 |

The catalyst of stage b) can be in the form of balls, but it is most often in the form of extrudates. It consists of an acid solid mixed with an amorphous phase like the catalyst of stage a).

The acid solid in question is shaped using a matrix, which is an amorphous phase. The acid solid is preferably at least one zeolite.

The FAU-structural-type zeolites and more particularly the Y zeolite, the MOR-structural-type zeolites (mordenite zeolite) that are synthesized in basic classic medium or else in fluoride medium (reference Patent IFP), the EUO-structural-type zeolites, i.e., the EU-1, ZSM-50, TPZ-3 zeolites), the NU-87 zeolite of the NES structural type will preferably be selected. All of these zeolites are described in the document "Atlas of Zeolite Structure Types," W. M. Meier, D. H. Olso and Ch. Baerlocker, 1996 Elsefier. Among the preferred and usable zeolites in the catalyst, the NU-86 zeolite that is described in Patent EP 463 768 A, the NU-85 zeolite that is described in Patent EP 462 745 A, the NU-88 zeolite that is described (French filing 96/10,507) and the IM-5 zeolite that is described in The patent (French filing 96/12,873) are also present. The zeolites are at least in part in acid form (H') but can also contain cations other than H' such as alkalines and alkaline-earths.

The zeolite content in the catalyst is between 5 and 95% by weight, preferably between 10 and 90% relative to the final catalyst. The overall Si/Al ratio of these zeolites is between 2.6 and 200, preferably between 5 and 100, and even more preferably between 5 and 80.

The matrix of the catalyst is a substrate that is selected from, for example, the group that is formed by alumina, silica, and silica-alumina, alumina-boron oxide, magnesia, silica-magnesia, zirconia, titanium oxide, clay, whereby these compounds are used alone or in mixtures. An alumina substrate is preferably used.

The B.E.T. surface area of catalyst No. 2 that is used in stage b) is between 30 and 900 m²/g, preferably between 150 and 500 m²/g. The Na/Al ratio of the final catalyst is less than 5% atomic and preferably less than 2%.

As for catalyst No. 1, the zeolite optionally can be doped by a promoter that is selected from among metal elements, such as, for example, the metals of the family of rare earths, in particular lanthanum and cerium, or the metals of group VIB of the periodic table, such as molybdenum, or noble or non-noble metals of group VIII, such as platinum, palladium, ruthenium, rhodium, iridium, iron and other metals such as manganese, zinc, and magnesium.

Figure 2:
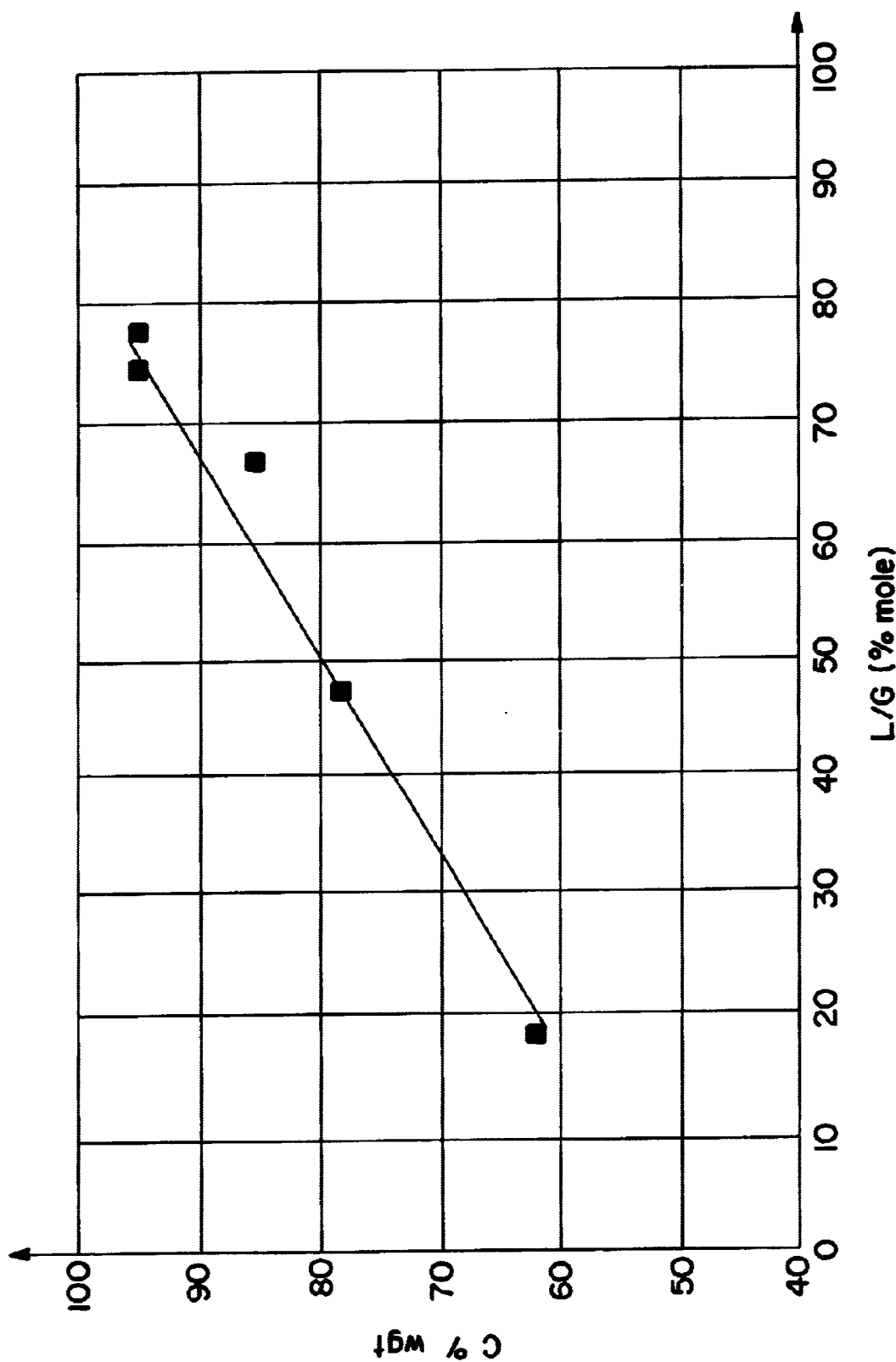
FIG. 2 is a graph of the percent weight conversion of the aromatic compounds (% weight) as a function of the liquid/gas mol ratio at the inlet (L/G mol).

Stages a and b, for example, are carried out under the following operating conditions. The pressure is between 2 bar and 90 bar, but preferably between 5 and 60 bar. The pressure should advantageously be the highest possible, since it makes it possible for the reaction to take place in liquid phase. FIG. 2 shows that there is a direct connection between the disappearance of the alkylating agent due to the alkylation of the aromatic compound (or conversion) and the gas/liquid ratio at the inlet of the reactor. In FIG. 2, the alkylating agent is decene-1.

The temperatures of catalysts No. 1 and No. 2 are generally between 30° C. and 300° C. and preferably between 60 and 250° C. The temperature has a favorable influence on the kinetics of the alkylation reaction.

The hourly volumetric flow rate that is the ratio of the flow rate of feedstock to the volume of catalyst can be between $0.1 m^3/m^3/h$ and $100 m^3/m^3/h$ and preferably between 0.1 and $10 m^3/m^3/h$.

The aromatic compound/alkylating agent ratio is, for example, between 0.1 mol/mol and 20 mol/mol and preferably between 0.1 mol/mol and 10 mol/mol. The aromatic compound/alkylating agent molar ratio has an influence on the structure of the products. Table 2 shows 100 weight% conversion of olefin (decene-1); and the yields of mono- and dialkyl benzene vary according to the benzene/decene-1 molar ratio.

The catalyst that is used in this case is catalyst A (Table 1).

TABLE 2

Influence of the Benzene/Olefin Molar Ratio on the Yields of Mono- and Dialkyl Benzene

| Benzene/olefin molar ratio | 11.04 | 9.04 | 5.66 | 2.92 | 1 | 0.5 |
|---|---|---|---|---|---|---|
| Material balances (% by weight) | | | | | | |
| Benzene (% by weight) | 76.9 | 74.4 | 63.3 | 43.1 | 17 | 9 |
| Monoalkyl (% by weight) | 22.2 | 24.1 | 33 | 46.2 | 60 | 64 |
| Dialkyl (% by weight) | 0.9 | 1.5 | 3.7 | 10.7 | 23 | 27 |
| Olefin conversion (% by weight) | 100 | 100 | 100 | 100 | 100 | 100 |
| Monoalkyl selectivity (%) | 96.1 | 94.1 | 89.9 | 81.2 | 72.9 | 70.3 |
| Dialkyl selectivity (%) | 3.9 | 5.9 | 10.1 | 18.8 | 27.7 | 29.7 |

Below are presented some examples of the process that make it possible to better understand its operation. In these examples, two olefins are used. They are decene-1 and octadecene-1. These compounds can, based on requirements, be replaced by any olefin that comprises 2 to 20 carbon atoms.

EXAMPLE 1

It is desired to produce C10 monoalkyl benzenes and dialkyl benzenes together with a C10 chain and a C18 chain.

The first reactor contains 100 $m^3$ of catalyst D (see Table No. 1), consisting of 70% of Nu-87 zeolite and 30% alumina. This reactor operates at a pressure of 40 bar with a flow rate of 100 $m^3$ of feedstock per hour. The feedstock consists of 48.86 tons of benzene and 35.08 tons of decene-1 which corresponds to a benzene to olefin molar ratio of 2.5 mol per mol. Catalyst D operates at a temperature of 190° C.

The products that exit from stage a) consist of:
18.96 tons of decene-1,
39.81 tons of benzene,
and 25.18 tons of C10 monoalkyl benzene.

Benzene and decene are recycled at the inlet of the reactor. Supplies of benzene (9.056 tons) and decene-1 (16,124 tons) will be carried out to allow the unit to operate continuously.

For the monoalkyls, two choices are possible. If it is not desired to produce dialkyl benzenes, the second reactor is stopped and the product is stored.

Otherwise, the 25.18 tons of monoalkyl is then sent into stage b).

These alkyls are mixed with 23.12 tons of octadecene-1, which corresponds to an alkyl/olefin molar ratio of 1.26 mol/mol. The mixture is sent into the second reactor that operates with catalyst B (see Table No. 1), consisting of 80% mordenite and 20% alumina. The operating pressure is 60 bar and the temperature of the catalyst is 210° C. The hourly volumetric flow rate is 1 $m^3/m^3/h$.

The products that exit stage b) after separation and distillation consist of:
20.6 tons of octadecene-1,
22.9 tons of C10 monoalkyl benzene,
4.8 tons of C10–C18 dialkyl benzene.

Octadecene-1 can be recycled at the inlet of the second reactor after an addition of 2.52 tons.

Table 3 presents the material balance of the products that enter the unit and the products that exit:

TABLE 3

Material Balance of the Consumed Reagents and Products of the Process

| | Consumed Reagents (tons/h) | Products (tons/h) |
|---|---|---|
| Benzene | 9.056 | |
| Decene-1 | 16.124 | |
| Octadecene-1 | 2.52 | |
| Monoalkyl benzene (C10) | | 22.9 |
| Dialkyl benzene (C10–C18) | | 4.8 |
| Total | 27.7 | 27.7 |

EXAMPLE 2

It is desired to produce C10 monoalkyl benzenes and two different types of dialkyls together:
dialkyl benzenes with two C10 chains,
dialkyl benzenes with a C10 chain and a C18 chain.

The first reactor contains catalyst 3, consisting of 80% mordenite and 20% alumina. This reactor operates at a pressure of 60 bar with a flow rate that makes it possible to obtain an hourly volumetric flow rate of 1 $m^3/m^3/h$. The feedstock consists of 48.86 tons of benzene and 35.08 tons of decene-1, which corresponds to a benzene to olefin molar ratio of 2.5 mol per mol. Catalyst D operates at a temperature of 180° C.

The products that exit stage a) consist of:
0.09 tons of decene1,
35.43 tons of benzene,
20.31 tons of C10 monoalkyl benzene,
28.12 tons of C10 dialkyl (C10–C10).

The benzene and decene are recycled at the inlet of the reactor. Additions of benzene (13,436 tons) and decene-1 (34,994 tons) will be carried out to allow the unit to operate continuously.

If it is desired to produce only monoalkyls and dialkyls, the second reactor is stopped, and the products are stored. If only the monoalkyls are desired, the C10–C10 dialkyls are recycled at the inlet of the first reactor to undergo a transalkylation with benzene.

If these are only symmetrical dialkyl benzenes that are desired, the monoalkyls are recycled at the inlet of the first reactor to undergo a second alkylation.

Otherwise, the 28.12 tons of C10–C10 dialkyls is stored. The 20.31 tons of monoalkyls is then sent into stage b). These alkyls are mixed with 18.64 tons of octadecene-1, which corresponds to an alkyl/olefin molar ratio of 1.26 mol/mol. The mixture is sent into the second reactor that operates with catalyst B, consisting of 80% mordenite and 20% alumina. The operating pressure is 60 bar, and the temperature of the catalyst is 210° C. The hourly volumetric flow rate is 1 $m^3/m^3/h$.

The products that exit stage b) after separation and distillation consist of:

16.55 tons of octadecene-1, 18.50 tons of C10 monoalkyl benzene, 3.9 tons of C10–C18 dialkylbenzene.

Octadecene-1 can be recycled at the inlet of the second reactor after an addition of 2.09 tons.

Table 4 presents the material balance of the products that enter the unit and the products that exit.

TABLE 4

Material Balance of the Process in Example 2.

| | Consumed Reagents (tons/h) | Products (tons/h) |
|---|---|---|
| Benzene | 13.436 | |
| Decene-1 | 34.994 | |
| Octadecene-1 | 2.09 | |
| Monoalkyl benzene (C10) | | 18.50 |
| Dialkyl benzene (C10—C10) | | 28.12 |
| Dialkyl benzene (C10–C18) | | 50.52 |
| Total | 50.52 | 27.7 |

The preceding examples can be repeated with similar success by substituting the generically or specifically described reactants and/or operating conditions of this invention for those used in the preceding examples. Also, the preceding specific embodiments are to be construed as merely illustrative, and not limitative of the remainder of the disclosure in any way whatsoever.

The entire disclosure of all applications, patents and publications, cited above and below, and of corresponding French application 00/05.677, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the production of monoalkyl aromatic compounds, dialkyl aromatic compounds, and trialkyl aromatic compounds in which the alkyl chains can be of the same or different length comprising:

reacting in a first alkylation reaction zone an aromatic compound and a first olefinic alkylating agent to produce a first effluent;

separating said first effluent into
a) an unreacted aromatic compound stream,
b) an unreacted first olefinic alkylating stream,
c) a first monoalkyl aromatic fraction, and
d) a first dialkyl aromatic fraction wherein the two alkyl chains are of the same length;

removing a portion of said first monoalkyl aromatic fraction as a product stream, removing at least a portion of said dialkyl aromatic fraction as a product stream, or both;

reacting in a second alkylation reaction zone at least a portion of said first monoalkyl aromatic fraction with a second olefinic alkylating agent to produce a second effluent;

separating said second effluent into
a) an unreacted monoalkyl aromatic fraction,
b) a second dialkyl aromatic fraction, and
c) a first trialkyl aromatic fraction; and removing at least a portion of said unreacted monoalkyl aromatic fraction, at least a portion of said second dialkyl aromatic fraction, or at least a portion of said first trialkyl aromatic fraction as a product stream.

2. A process according to claim 1, wherein said first and second olefinic alkylating agents each comprise 2 to 20 carbon atoms.

3. A process according to claim 2, wherein the number of carbon atoms in said first olefinic alkylating agent is different from the number of carbon atoms in said second olefinic alkylating agent.

4. A process according to claim 1, comprising a gas/liquid separation between said first reaction zone and said separation of said first effluent.

5. A process according to claim 4, wherein said aromatic compound is benzene.

6. A process according to claim 5, wherein the second effluent from the second alkylation reaction zone is separated into a fourth fraction comprising unreacted second olefinic alkylating agent.

7. A process according to claim 5, wherein at least a portion of said first dialkyl aromatic fraction is recycled to said second alkylation reaction zone.

8. A process according to claim 4, wherein at least a portion of said first dialkyl aromatic fraction is recycled to said first alkylation reaction zone.

9. A process according to claim 4, wherein in each reaction zone, the molar ratio of aromatic compounds to alkylating agent is between 0.1 and 20 mol/mol.

10. A process according to claim 9, wherein said molar ratios are between 0.1 and 12 mol/mol.

11. A process according to claim 4, wherein said first and second alkylation reaction zones operate with catalysts of the same composition.

12. A process according to claim 11, wherein said first and second alkylation reaction zones operate under different operating conditions.

13. A process according to claim 4, wherein said first and second alkylation reaction zones operate with catalysts of different compositions.

14. A process according to claim 13, wherein operating pressures are between 2 and 100 bars, and operating temperatures are between 10 and 300° C.

15. A process according to claim 14, wherein hourly volumetric flow rates are between 0.1 and 100 $m^3/m^3/h$.

16. A process according to claim 15, wherein said hourly volumetric flow rates are between 0.1 and 10 $m^3/m^3/h$.

17. A process according to claim 14, wherein the operating pressures are between 5 and 60 bars and the operating temperatures are between 60° and 250° C.

18. A process according to claim 13, wherein the catalysts are acidic solids.

19. A process according to claim 18, wherein each of the catalysts contain between 5 and 95% by weight zeolite.

20. A process according to claim 19, wherein said the zeolite is faujasite, mordenite, EUO, EU-1, ZSM-50, TPZ-3, NU-87, NU-88, NU-86, or IM-5.

21. A process according to claim 20, wherein said zeolite is doped by at least one promoter selected from the group consisting of metals of the family of rare earths, metals of group VIB, noble metals, non-noble metals of group VIII, manganese, zinc and magnesium.

22. A process according to claim 21, wherein said at least one promoter is lanthanum, cerium, molybdenum, platinum, palladium, ruthenium, rhodium, iridium, iron, manganese, zinc or magnesium.

23. A process according to claim 13, wherein said first and second alkylation reaction zones operate under different operating conditions.

24. A process according to claim 1, wherein said second dialkyl aromatic fraction contains a dialkyl aromatic compound in which the alkyl portions are of different lengths.

25. A process according to claim 24, wherein said first trialkyl aromatic fraction contains a trialkyl aromatic compound in which the alkyl portions are not all of the same length.

26. A process according to claim 1, wherein said first trialkyl aromatic fraction contains a trialkyl aromatic compound in which the alkyl portions are not all of the same length.

27. A process according to claim 1, wherein separation if said first effluent is performed by fractionation and separation of said second effluent is performed by fractionation.

28. A process according to claim 27, wherein said first alkylation reaction zone and said second alkylation zone each contain a catalyst.

29. A process for the production of monoalkyl aromatic compounds, dialkyl aromatic compounds, and trialkyl aromatic compounds comprising:

reacting in a first alkylation reaction zone an aromatic compound and a first olefinic alkylating agent to produce a first effluent containing a first monoalkyl aromatic fraction;

reacting in a second alkylation reaction zone at least a portion of said first effluent containing a first monoalkyl aromatic fraction with a second olefinic alkylating agent to produce a second effluent;

separating said second effluent into
   a) an unreacted monoalkyl aromatic fraction,
   b) a dialkyl aromatic fraction, and
   c) a first trialkyl aromatic fraction; and
     removing a portion of said unreacted monoalkyl aromatic fraction, at least a portion of said second dialkyl aromatic fraction, or at least a portion of said first trialkyl aromatic fraction as a product stream, wherein the number of carbon atoms in said first olefinic alkylating agent is different from the number of carbon atoms in said second olefinic alkylating agent.

30. A process according to claim 29, wherein said first and second alkylation reaction zones are in series, and the catalysts used in the first and second alkylation reaction zones each, independently, comprise at least one zeolite mixed with an amorphous phase selected from alumina, silica, silica-alumina, alumina-boron oxide, magnesia, silica-magnesia, zirconia, titanium oxide, and clay, and wherein the zeolite content of the catalyst is, in each case, 10–90 wt.%.

31. A process according to claim 1, wherein the number of carbon atoms in said first olefinic alkylating agent is different from the number of carbon atoms in said second olefinic alkylating agent.

* * * * *